(12) United States Patent
Eddy (10) Patent No.: US 8,449,483 B2
(45) Date of Patent: May 28, 2013

(54) COMPRESSION DEVICE AND CONTROL SYSTEM FOR APPLYING PRESSURE TO A LIMB OF A LIVING BEING

(76) Inventor: Patrick Eddy, Allendale, MI (US)

( * ) Notice: Subject to any disclaimer, the term of this patent is extended or adjusted under 35 U.S.C. 154(b) by 568 days.

(21) Appl. No.: 12/629,526

(22) Filed: Dec. 2, 2009

(65) Prior Publication Data

US 2010/0137764 A1 Jun. 3, 2010

Related U.S. Application Data

(60) Provisional application No. 61/221,650, filed on Jun. 30, 2009, provisional application No. 61/119,235, filed on Dec. 2, 2008.

(51) Int. Cl.
*A61H 7/00* (2006.01)
*A61H 19/00* (2006.01)

(52) U.S. Cl.
USPC ........... 601/152; 601/148; 601/149; 601/150; 601/151; 606/201; 606/202

(58) Field of Classification Search
USPC ............... 601/148–152; 602/13; 606/201, 606/202, 212
See application file for complete search history.

(56) References Cited

U.S. PATENT DOCUMENTS

| | | | |
|---|---|---|---|
| 1,646,590 A * | 10/1927 | Mildenberg | 601/151 |
| 3,862,629 A | 1/1975 | Rotta | |
| 3,888,242 A * | 6/1975 | Harris et al. | 601/152 |
| 3,892,229 A * | 7/1975 | Taylor et al. | 601/152 |
| 3,896,794 A * | 7/1975 | McGrath | 601/152 |
| 3,933,150 A * | 1/1976 | Kaplan et al. | 601/151 |
| 3,976,056 A * | 8/1976 | Brawn | 601/152 |
| 4,029,087 A * | 6/1977 | Dye et al. | 601/152 |
| 4,520,819 A * | 6/1985 | Birmingham et al. | 606/202 |
| 4,738,249 A * | 4/1988 | Linman et al. | 601/152 |
| 4,865,020 A * | 9/1989 | Bullard | 601/152 |
| 5,109,832 A * | 5/1992 | Proctor et al. | 601/149 |
| 5,263,473 A | 11/1993 | McWhorter | |
| 5,428,078 A * | 6/1995 | Cohen et al. | 522/2 |
| 5,626,556 A | 5/1997 | Tobler et al. | |
| 5,674,262 A | 10/1997 | Tumey | |
| 5,796,312 A | 8/1998 | Dye | |
| 6,007,559 A | 12/1999 | Arkans | |
| 6,036,718 A * | 3/2000 | Ledford et al. | 606/202 |

(Continued)

OTHER PUBLICATIONS

Michigan Medical Innovations, LLC, DVTCare (http://michmedical.com/dvt_pump_overview/need_dvt.htm), Date: Mar. 1, 2010.

*Primary Examiner* — Clinton T Ostrup
*Assistant Examiner* — Michael Tsai
(74) *Attorney, Agent, or Firm* — Price Heneveld LLP (57) ABSTRACT

A device to compress the limb of a living being includes a user interface, a programmable logic controller, a power source, a source of fluidic pressure, valves with ports in fluidic connection with the source of fluidic pressure, other valves, and a first and second inflatable bladders, wherein the programmable logic controller is programmed to cause the repeating sequence of inflating the first inflatable bladder by manipulating the ports of the valves, after a first preset period of time, deflating the first inflatable bladder and allowing the pressure within the first inflatable bladder to inflate partially the second inflatable bladder by manipulating the ports of the valves. The source of fluidic pressure can be a self-contained pump, a connection to fluidic pressure in a health care facility, or a pressurized canister. The power source can be a battery. The device may extend the life of the power source.

12 Claims, 5 Drawing Sheets

U.S. PATENT DOCUMENTS

| | | |
|---|---|---|
| 6,080,120 A | 6/2000 | Sandman et al. |
| 6,224,579 B1 * | 5/2001 | Modak et al. ............... 604/265 |
| 6,231,532 B1 | 5/2001 | Watson et al. |
| 6,544,202 B2 | 4/2003 | McEwen et al. |
| 6,786,879 B1 | 9/2004 | Bolam et al. |
| 6,866,859 B2 * | 3/2005 | Trogolo et al. ............... 424/423 |
| 2002/0115949 A1 | 8/2002 | Kuslich et al. |
| 2003/0139255 A1 | 7/2003 | Lina |
| 2005/0070828 A1 | 3/2005 | Hampson et al. |
| 2005/0187503 A1 | 8/2005 | Tordella et al. |
| 2005/0203452 A1 | 9/2005 | Weston et al. |
| 2005/0222526 A1 | 10/2005 | Perry et al. |
| 2005/0242644 A1 * | 11/2005 | Bauer et al. ............... 297/284.3 |
| 2006/0004245 A1 | 1/2006 | Pickett et al. |
| 2007/0135743 A1 | 6/2007 | Meyer |
| 2007/0161933 A1 | 7/2007 | Ravikumar |
| 2007/0167884 A1 | 7/2007 | Mangrum et al. |
| 2007/0179416 A1 | 8/2007 | Obrien et al. |
| 2008/0249442 A1 * | 10/2008 | Brown et al. ............... 601/152 |
| 2010/0268130 A1 * | 10/2010 | Khan ............... 601/46 |

\* cited by examiner

COMPRESSION DEVICE AND CONTROL SYSTEM FOR APPLYING PRESSURE TO A LIMB OF A LIVING BEING

CROSS-REFERENCE TO RELATED APPLICATIONS

This application claims the benefit of U.S. Provisional Application No. 61/221,650, filed Jun. 30, 2009, and U.S. Provisional Application No. 61/119,235, filed Dec. 2, 2008. Both said provisional applications are incorporated herein in their entireties.

BACKGROUND

The present invention generally relates to a compression device for treating various circulatory disorders and generally improving circulation for users such as athletes, people with wounds, and people who have to sit for a long period of time. More specifically the present invention relates to a compression device with inflatable bladders and a control system for applying compressive pressure to a body part of a living being.

The inventive compression device may be used to treat any or all of the following circulatory disorders: deep vein thrombosis (DVT), lymphedema, chronic venous insufficiency (CVI), varicose veins, and peripheral arterial disease (PAD).

Deep Vein Thrombosis is a blood clot that can form in a person's legs and sometimes move to his or her lungs, where it could potentially be fatal. DVT is usually caused by immobility. DVT is commonly treated with compression devices. The inventive compression device may be used in DVT prevention, although a user should consult a physical before doing so, as any compression device could release a dangerous blood clot.

DVT kills 200,000 Americans each year, more than AIDS and breast cancer combined. 74% of Americans do not know of the condition or symptoms. This little known condition hospitalizes 600,000 people each year. About 2 million people in the United States have a pulmonary embolism each year and more than 10% die from it. Nine out of ten cases of pulmonary embolism are caused by blood clots that form in the legs and then travel to the lungs. Most who die from DVT do so within 30-60 minutes after symptoms start. Pulmonary embolisms occur equally in men and women. The risk of having a pulmonary embolism doubles for every 10 years after the age of 60.

Lymphedema is an abnormal build up of lymph fluid which occurs when a lymph system becomes blocked or impaired. Usually, the affected area involves an extremity. Lymphedema causes the extremity to swell and become heavy and limited in mobility and function. Lymphedema is commonly treated with compression devices. Primary lymphedema is present at birth and effects 2,000,000 people worldwide, effects 10 women to every 1 man, and effects 10 legs to every 1 arm.

Secondary lymphedema is caused by scarring, injury to, or removal of lymph nodes. Secondary lymphedema affects 25,000,000 people worldwide and 2.5 million in the United States.

Chronic venous insufficiency (CVI) is a condition where blood pools in the veins of the lower legs. The veins return blood to the heart from all the body's organs. To do this the calf muscles and the muscles in the feet need to contract with each step to squeeze the veins and push the blood upward. To keep the blood flowing up, and not back down, the veins contain one-way valves. Chronic venous insufficiency occurs when these valves become damaged, allowing the blood to leak backward and pool. Massage techniques are currently used for treatment, along with pressure stockings and compression. Sometimes bypass surgery or valve repair is required.

CVI is a significant public health problem in the United States. About 2-5% of all Americans have change associated with CVI. Approximately 24 million Americans have varicose veins and approximately 6 million Americans have skin changes associated with CVI. Venous stasis ulcers affect approximately 500,000 people. The mean incidence for hospital admission for CVI is 92 per 100,000 admissions. CVI can lead to leg ulcers which can be severe and are responsible for 100,000 cases of disability in the United States alone. Incidences of CVI typically occur in women aged 40-49 and men aged 70-79.

Varicose veins are swollen veins that you can see through the skin. They often look blue, bulging, and twisted. Left untreated, varicose veins may worsen over time. Large varicose veins can cause aching and feelings of fatigue as well as skin changes like rashes, redness, and sores. There are three kinds of veins in a person's legs: the superficial veins, which lie closest to the skin, the deep veins, which lie in groups of muscles, and perforating veins, which connect the superficial veins to the deep veins. The deep veins lead to the vena cava, the body's largest vein, which runs directly to the heart. Varicose veins occur in the superficial veins in your legs.

When a person is in the upright position, the blood in his or her leg veins must work against gravity to return to the heart. To accomplish this, the leg muscles squeeze the deep veins of the legs and feet. One-way flaps, called valves, in the veins keep blood flowing in the right direction. When the leg muscles contract, the valves inside the veins open. When the legs relax, the valves close. This prevents blood from flowing in reverse, back down the legs. The entire process of sending blood back to the heart is called the venous pump. Varicose veins are commonly treated with compression devices, sclerotherapy, ablation, laser treatment, or vein stripping.

As many as 40 million Americans, most of them women, have varicose veins. 50% of all women will suffer from varicose veins by their mid-50's.

When the arteries in the legs become blocked, the legs do not receive enough blood or oxygen. This may be due to a condition called peripheral artery disease (PAD), sometimes called leg artery disease. PAD is commonly treated by lifestyle changes, compression devices, medication, exercise, angioplasty/stenting, bypass surgery, endarterectomy, or amputation. One in three people age 70 or older has PAD. PAD affects about 8 million Americans. Persons with PAD also have four to five times higher risk of a heart attack or stroke.

The above conditions affect tens of millions of people. One common treatment opportunity is using compression devices. Currently there are several antiquated and differing compression devices for each condition.

The inventor has recognized that certain embodiments of the compression devices disclosed herein can treat all of these conditions. In addition, the compression devices disclosed herein can be used for preventative purposes, such as when the user has to sit for a long period of time, like on an airplane. In addition, the compression device disclosed herein can be used in sports medicine, as a circulatory assistant (a) to improve removal of lactic acid after a workout by improving circulation; (b) to promote healing and recovery time after workouts by minimizing muscle micro-hemorrhaging; (c) to increase circulation to reduced blood pooling and provide nourishment and oxygen to stressed muscles; and (d) to reduce the chance for cramping. Moreover, the compression devices disclosed herein can be used to treat and prevent chronic wounds, especially wounds that are subsisting because of poor circulation (like venous ulcer), because healing such wounds can benefit from enhanced circulation.

One prior art compression device is disclosed in U.S. Pat. No. 6,786,879. This device includes a control unit that includes an air compressor and a valve manifold that is controlled by a microprocessor. The microprocessor may control the valves in several different operating modes. The operating mode is selected depending upon the different compression sleeves to which the control unit is connected. Up to two compression sleeves may be simultaneously connected to the control unit where each compression sleeve may have four chambers. Eight valves in the control unit are coupled to the four chambers of each of the two compression sleeves using eight tubes. With four tubes running to each compression sleeve, there is an increased likelihood of getting the tubes tangled or pinched. Each of the valves is discreetly electrically coupled to the microprocessor. Different compression sleeves are used for each form of treatment.

SUMMARY OF THE INVENTION

Described herein are several embodiments of an apparatus that can compress a body part of a living being, such as to cause blood flow within the body part in a given direction. A method of using the apparatus to compress a body part of a living being, such as to cause blood flow within the limb in a given direction is additionally described herein.

More specifically, described herein is a compression device comprising a user interface, a programmable logic controller in electronic connection with the user interface, a battery power source in electronic connection with the programmable logic controller, a source of fluidic pressure in electronic connection with the battery power source and the programmable logic controller, a first valve having at first port in fluidic connection with the source of fluidic pressure and a second port in fluidic connection with a first inflatable bladder, a second valve having a first port in fluidic connection with the source of fluidic pressure and a second port in fluidic connection with a second inflatable bladder. The programmable logic controller is programmed to cause a repeating sequence of inflating the first inflatable bladder by opening the first and second ports of the first valve, closing the first and second ports of the second valve, and activating the source of fluidic pressure, then after a first period of time, deflating the first inflatable bladder by deactivating the source of fluidic pressure, inflating the second inflatable bladder by closing the first and second ports of the first valve, opening the first and second ports of the second valve, and activating the source of fluidic pressure, waiting for a second period of time, then deflating the second inflatable bladder by deactivating the source of fluidic pressure. The user interface allows the user to select a mode that extends the life of the battery power source by selecting the first period of time and the second period of time such that the life of the battery will last for a desired time.

In addition, described herein is a compression device comprising a user interface, a programmable logic controller in electronic connection with the user interface, a power source in electronic connection with the programmable logic controller, a source of fluidic pressure in electronic connection with the power source (if the electronic connection is needed) and the programmable logic controller, a first valve having at first port in fluidic connection with the source of fluidic pressure, a second port in fluidic connection with a first inflatable bladder, and a third port in fluidic connection with a second valve. The second valve has a first port in fluidic connection with the source of fluidic pressure, a second port in fluidic connection with a second inflatable bladder, and a third port in fluidic connection with the first valve. The programmable logic controller is programmed to cause the repeating sequence of: (a) inflating the first inflatable bladder by opening the first and second ports of the first valve, closing the third port of the first valve, closing the first and second ports of the second valve, and activating the source of fluidic pressure; (b) after a first period of time, deflating the first inflatable bladder and partially inflating the second inflatable bladder by deactivating the source of fluidic pressure, closing the first port of the first valve, opening the third port of the first valve, opening the third port of the second valve, and opening the second port of the second valve; (c) further inflating the second inflatable bladder by closing the first, second, and third ports of the first valve, opening the first and second ports of the second valve, closing the third port of the second valve, and activating the source of fluidic pressure; and (d) after a second period of time, deflating the second inflatable bladder and partially inflating the first inflatable bladder by deactivating the source of fluidic pressure, closing the first port on the second valve, opening the third port of the second valve, opening the third port of the first valve, and opening the second port of the first valve. In this manner, the fluid pressure within the first inflatable bladder, when allowed to deflate, partially inflates the second inflatable bladder (and vice-versa), thus requiring less work by the source of fluidic pressure and the power source.

In addition, described herein is a compression device comprising a user interface, a programmable logic controller in electronic connection with the user interface, and a housing. The housing at least partially houses the user interface and the programmable logic controller, and comprises an antimicrobial substance.

In addition, described herein is a compression device comprising an inflatable bladder and a cuff at least partially surrounding the inflatable bladder. The cuff comprises an antimicrobial substance.

In addition, described herein is a compression device comprising an inflatable bladder including an inlet port and an interior volume. The inlet port is in fluidic communication with the interior volume. The interior volume comprises a first chamber, a second chamber, and a third chamber. The first chamber is in fluidic communication with the inlet port and the second chamber. The second chamber is in fluidic communication with the third chamber. The first divider partially separates the first chamber from the second chamber. The second divider partially separates the second chamber from the third chamber.

In addition, described herein is a method of compressing a body part comprising the steps of: (a) presenting a compression device; (b) at least partially surrounding a body part of a living being with the compression device; and (c) using the source of fluidic pressure to inflate the inflatable bladder. The compression device comprises an inflatable bladder. The inflatable bladder comprises an inlet port and an interior volume, the inlet port being in fluidic communication with the interior volume and a source of fluidic pressure. The interior volume comprises a first chamber, a second chamber, and a third chamber, the first chamber in fluidic communication with the second chamber, and the second chamber in fluidic communication with the third chamber. A first divider partially separates the first chamber from the second chamber. A second divider partially separates the second chamber from the third chamber. This method can also be used to treat or prevent a chronic wound by enhancing circulation (in addition to the other purposes described above).

In addition, described herein is a compression device comprising an inflatable bladder. The inflatable bladder comprises an inlet port in fluidic communication with a source of fluidic pressure. The inflatable bladder further comprises a first chamber, a second chamber, a third chamber, a first check valve, and a second check valve. The first chamber is in fluidic communication with the inlet port and the second chamber, through a first check valve. The second chamber is in fluidic communication with the third chamber, through a second check valve.

In addition, described herein is a method of compressing a body part comprising the steps of: (a) presenting a compression device; (b) at least partially surrounding a body part of a living being with the compression device; and (c) using the source of fluidic pressure to inflate the inflatable bladder. The compression device comprises an inflatable bladder. The inflatable bladder comprises an inlet port in fluidic communication with a source of fluidic pressure. The inflatable bladder further comprises a first chamber, a second chamber, a third chamber, a first check valve, and a second check valve. The first chamber is in fluidic communication with the inlet port and the second chamber, through a first check valve. The second chamber is in fluidic communication with the third chamber, through a second check valve. The first check valve and the second check valve are capable of causing the first chamber to inflate fully before the second chamber inflates fully, and the second chamber to inflate fully before the third chamber inflates fully. This method can also be used to treat or prevent a chronic wound by enhancing circulation (in addition to the other purposes described above).

In addition, described herein is a compression device comprising a primary valve including an inlet port in fluidic communication with a source of fluidic pressure, and an outlet port in fluidic communication with a manifold. The compression device further comprises a first bladder including a port in fluidic connection with a first valve, the first valve in fluidic connection with the manifold. The compression device further comprises a second bladder including a port in fluidic connection with a second valve, the second valve in fluidic connection with the manifold. The compression device further comprises a third bladder including a port in fluidic connection with a third valve, the third valve in fluidic connection with the manifold. The compression device further comprises a cuff at least partially housing the first bladder, the second bladder, and the third bladder. The compression device further comprises a primary logic controller capable of selectively controlling the opening and closing of the first valve, the second valve, and the third valve.

In addition, described herein is a method of compressing a body part comprising the steps of (a) presenting a compression device and (b) at least partially surrounding a body part of a living being with the compression device. The compression device comprises a primary valve including an inlet port in fluidic communication with a source of fluidic pressure, and an outlet port in fluidic communication with a manifold. The compression device further comprises a first bladder including an inlet port in fluidic connection with a first inlet valve, the first inlet valve in fluidic connection with the manifold. The compression device further comprises a second bladder including an inlet port in fluidic connection with a second inlet valve, the second inlet valve in fluidic connection with the manifold. The compression device further comprises a third bladder including an inlet port in fluidic connection with a third inlet valve, the third inlet valve in fluidic connection with the manifold. The compression device further comprises a cuff at least partially housing the first bladder, the second bladder, and the third bladder. The compression device further comprises a primary logic controller capable of selectively controlling the opening and closing of the first inlet valve, the second inlet valve, and the third inlet valve. This method can be used to treat or prevent a chronic wound by enhancing circulation, including directing blood flow towards the chronic wound (or where a chronic wound may be developing) (in addition to the other purposes described above).

In addition, herein described is a method of treating a wound comprising the steps of: (i) presenting a body part of a living being, the body part having a wound and an area adjacent to the wound; (ii) presenting a compression device comprising an inflatable bladder in fluid communication with a source of fluidic pressure; (iii) at least partially surrounding the area of the body part adjacent to the wound with the compression device; and (iv) using the source of fluidic pressure to inflate the inflatable bladder to increase circulation in the body part.

DETAILED DESCRIPTION OF THE PREFERRED EMBODIMENTS

Figure 1:
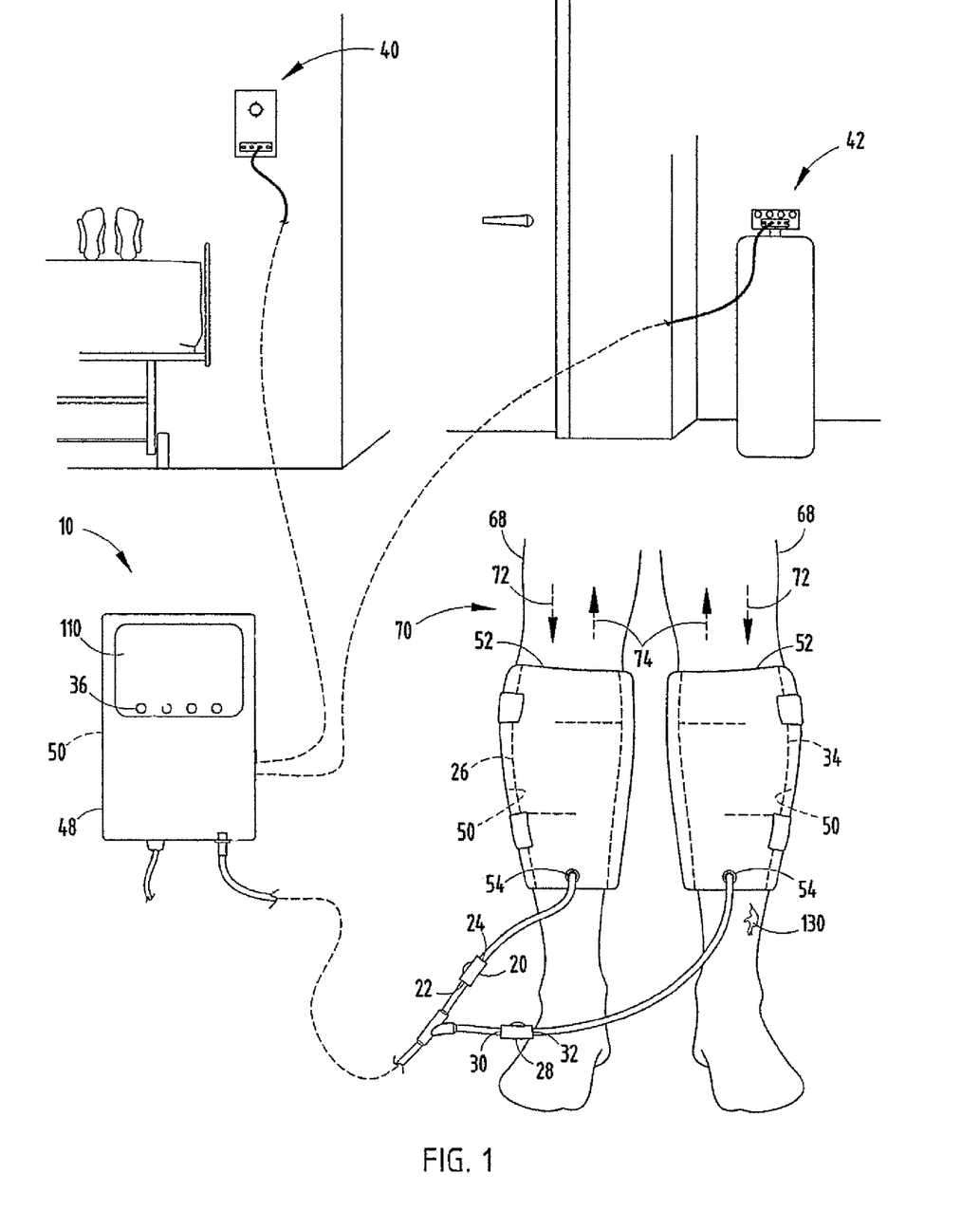
FIG. 1 depicts a perspective view of a first embodiment of compression device 10 attached to the body part 68 of a living being 70 and alternate sources of fluidic pressure.

For purposes of description herein, the terms "upper," "lower," "right," "left," "rear," "front," "vertical," "horizontal," and derivatives thereof shall relate to the invention as oriented in FIG. 1. However, it is to be understood that the invention may assume various alternative orientations and step sequences, except where expressly specified to the contrary. It is also to be understood that the specific devices and processes illustrated in the attached drawings, and described in the following specification are exemplary embodiments of the inventive concepts defined in the appended claims. Hence, specific dimensions and other physical characteristics relating to the embodiments disclosed herein are not to be considered as limiting, unless the claims expressly state otherwise.

In a first embodiment, compression device 10 (FIGS. 1 and 2) generally comprises a housing 48 for a user interface 12, a programmable logic controller 14, access to a power source 16 (such as a battery), and access to a source of fluidic pressure 18. The user interface 12 can provide a data display 110 to inform the user of important data such as battery life, pressure settings, and timing intervals. The user interface 12 can have buttons or a pressure sensitive screen to allow the user to select various operating modes, set variables, such as pressures, timing intervals, and the order in which specific inflatable bladders (discussed below) will be inflated and/or deflated. The user interface 12 is in electronic connection with the programmable logic controller 14 and the power source 16. For example, the user interface 12 can have a button or pressure sensitive touch option that, when pressed, communicates with the programmable logic controller 14. As a consequence, the user interface can command the programmable logic controller 14 to take steps to extend the life of the power source 16 (especially when the power source is a battery housed within housing 48), as discussed in greater detail below.

The source of fluidic pressure 18 can be a pump 38, which the housing 48 can house, or a source external to the housing 48. The source of fluidic pressure 18 can be in electronic connection with power source 16 (FIG. 2), such as when the source of fluidic pressure 18 is a pump 38 housed within housing 48 and the power source 16 is a battery also housed within housing 48. The source of fluidic pressure 18 can be in electronic connection with the programmable logic controller 14, such as when the source of fluidic pressure 18 is a pump 38 housed within housing 48 (FIG. 3). As alternatives or in addition to the pump 38, the source of fluidic pressure 18 can be a connection in a health care facility 40 (FIG. 1) (such as an oxygen, air, carbon dioxide, or nitrogen supply) or a pressurized canister 42 (containing a gas such as oxygen, air, carbon dioxide, or nitrogen).

In this first embodiment, compression device 10 further comprises a first valve 20 (FIG. 1) and a second valve 28. The first valve 20 has a first port 22 in fluidic connection with the source of fluidic pressure 18 and a second port 24 in fluidic connection with a first inflatable bladder 26. The second valve 28 has a first port 30 in fluidic connection with the source of fluidic pressure and a second port 32 in fluidic connection with a second inflatable bladder 34. Although shown in FIG. 1 as including first and second valves 20 and 28 external to the housing 48 for controller 14, first and second valves 20 and 28 may be located internally within housing 48 such that one tube runs from housing 48 to inflatable bladder 26 and another tube runs from housing 48 to inflatable bladder 34.

The programmable logic controller 14 is in electronic connection with the first valve 20 and the second valve 28 and thereby can control the opening and closing the valves 20 and 28. As a consequence, the programmable logic controller 14 controls the inflation of the first inflatable bladder 26 and the second inflatable bladder 34. The programmable logic controller 14 can be programmed to cause the repeating sequence of: (i) inflating the first inflatable bladder 26 by opening the first 22 and second 24 ports of the first valve 20, closing the first 30 and second ports 32 of the second valve 28, and activating the source of fluidic pressure 18; (ii) after a first period of time, deflating the first inflatable bladder 26 by deactivating the source of fluidic pressure 18; (iii) inflating the second inflatable bladder 34 by closing the first 22 and second 24 ports of the first valve 20, opening the first 30 and second 32 ports of the second valve 28, and activating the source of fluidic pressure 28; and (iv) after a second period of time, deflating the second inflatable bladder 34 by deactivating the source of fluidic pressure 18.

In this first embodiment, the user interface 12 allows the user to select a mode 36 (FIG. 1), such as an air-flight mode, that extends the life of the power source 16 (for example, a battery) by selecting the first period of time or the second period of time or both such that the battery charge will last for a selected period of time (i.e., the duration of the flight). After selecting the mode 36 (or in conjunction with selecting the mode 36), the user interface 12 can prompt or allow the user to input a total time of usage and the programmable logic controller 14 would then automatically measure the power remaining in the power source 16, calculate the first period of time and the second period of time, and utilize the calculated first period of time and second period of time in the repeating sequence. Extending the first preset period of time and/or the second present period of time delays the need for the power source 16 to use power to open the aforementioned ports of the aforementioned valves and to activate the source of fluidic pressure 18. Mode 36 that extends the life or charge of the power source 16 is useful when the user desires to use the compression device 10 for an extended period of time, such as on a long air flight, where access to a non-battery power source 16 is unavailable. The power source may include rechargeable or non-rechargeable batteries. The logic controller 14 may continuously monitor the charge of the batteries and readjust the first and second periods of time such that the batteries can operate the device over the entire length of the flight and so that the device will inflate the bladders 26 and 34 as often as possible without running the batteries down before the flight is over.

The housing 48 could optionally house sufficient memory to hold music and/or video and a display and speakers for playback so that the user could be entertained while using the compression device 10.

In a second embodiment, the compression device 10 comprises a user interface 12 (FIGS. 1 and 2), a programmable logic controller 14, a power source 16, and a source of fluidic pressure 18. The programmable logic controller 14 is in electronic connection with the user interface 12. The power source 16 is in electronic connection with the programmable logic controller 14. The power source 16 can be a battery. The source of fluidic pressure 18 is in electronic connection with the power source 16 (if needed to activate the source of fluidic pressure 18) and the programmable logic controller 14.

This embodiment of the compression device 10 further comprises a first valve 20 (FIG. 3), a first inflatable bladder 26, and a second valve 28. The first valve 20 has a first port 22 in fluidic connection with the source of fluidic pressure 18, a second port 24 in fluidic connection with the first inflatable bladder 26, and a third port 44 in fluidic connection with the second valve 28. The second valve 28 has a first port 30 in fluidic connection with the source of fluidic pressure 18, a second port 32 in fluidic connection with a second inflatable bladder 34, and a third port 46 in fluidic connection with the first valve 20. The source of fluidic pressure 18 can be a pump 38. As alternatives or in addition to the pump 38, the source of fluidic pressure can be a connection in a health care facility 40 (FIG. 1) (such as an oxygen, air, carbon dioxide, or nitrogen supply) or a pressurized canister 42 (containing a gas such as oxygen, air, carbon dioxide, or nitrogen). Although shown in FIG. 3 as including first and second valves 20 and 28 external to housing 48 for controller 14, first and second valves 20 and 28 may be located internally within housing 48 such that one tube runs from housing 48 to inflatable bladder 26 and another tube runs from housing 48 to inflatable bladder 34.

In this second embodiment (FIG. 3), the programmable logic controller 14 is programmed to cause the repeating sequence of: (i) inflating the first inflatable bladder 26 by opening the first 22 and second 24 ports of the first valve 20, closing the third port 44 of the first valve 20, closing the first 30 and second 32 ports of the second valve 28, and activating the source of fluidic pressure 18; (ii) after a first period of time, deflating the first inflatable bladder 26 and partially inflating the second inflatable bladder 34 by deactivating the source of fluidic pressure 18, closing the first port 22 of the first valve 20, opening the third port 44 of the first valve 20, opening the third port 46 of the second valve 28, and opening the second port 32 of the second valve 28; (iii) further inflating the second inflatable bladder 34 by closing the first 22, second 24, and third 44 ports of the first valve 20, opening the first 30 and second 32 ports of the second valve 28, closing the third port 46 of the second valve 28, and activating the source of fluidic pressure 18; and (iv) after a second period of time, deflating the second inflatable bladder 34 and partially inflating the first inflatable bladder 26 by deactivating the source of fluidic pressure 18, closing the first port 30 on the second valve 28, opening the third port 46 of the second valve 28, opening the third port 44 of the first valve 20, and opening the second port 24 of the first valve 20. In this way, one inflatable bladder (deflated relative to the other bladder) "scavenges" fluid pressure from the other bladder (inflated relative to the other bladder), because the higher relative pressure within the inflated bladder causes the inflated bladder to partially deflate and partially inflate the other bladder until the pressure within the two bladders are essentially in equilibrium. The first and second periods of time could be between 0 and 60 seconds, but could be longer.

In either embodiment, the housing 48 (FIGS. 1 and 2) can at least partially house the user interface 12 and the programmable logic controller 14, and the housing 48 can include an antimicrobial substance 50. For example, the antimicrobial substance 50 can include a substance that emits silver-ions, such as a plastic co-molded or co-extruded with a silver-ion emitter (like MCX 122656, manufactured by RTP Co., Winona, Minn.), or a plastic coated or plated with a silver-ion emitter. As other examples, the antimicrobial substance 50 can be one or more of 3 trimethoxysilylpropyloctadecyldimethyl ammonium chloride, hyaluronan and its derivatives, and triclosan. The emission of ions from substances such as the aforementioned aid in the destruction of microbes on a cellular level. Such ions need not necessarily be silver ions. The inflatable bladders 26 and 34 (FIG. 3) described in the above embodiments likewise can include such an antimicrobial substance 50.

In either embodiment, a cuff 52 (FIG. 3) can surround, enclose, or encompass the inflatable bladder (such as first inflatable bladder 26). The cuff 52 allows the user to attach the first inflatable bladder 26 to a body part 68 of the living being 70 (FIG. 1), so that inflation of the first inflatable bladder 26 compresses the body part 68 to which the cuff 52 is attached. The cuff 52 can include such an antimicrobial substance 50 (FIG. 3) described above. The body part 68\could be (but is not limited to) a calf and/or thigh. The cuff 52 can be made from a breathable material such as nylon but need not be.

Figure 4:
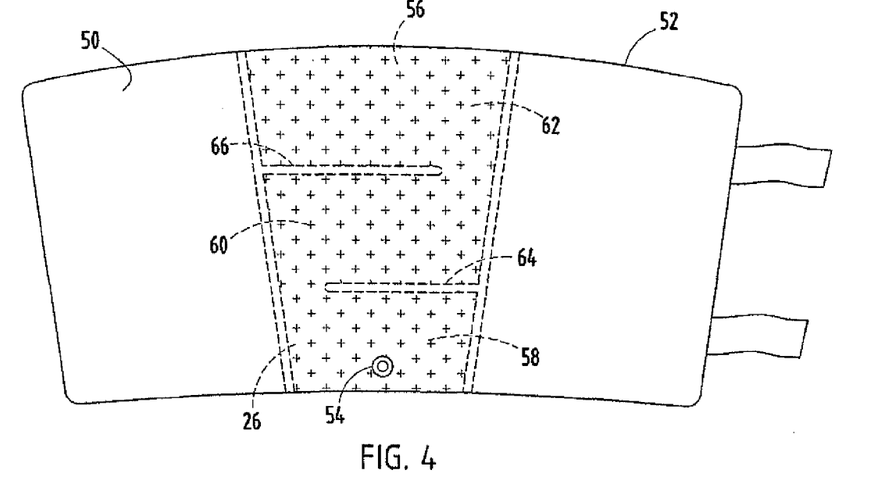
FIG. 4 depicts a front view of a first bladder 26 with three chambers.

In either embodiment (or with any other compression device), the inflatable bladder of the compression device 10, such as the first inflatable bladder 26, can include an inlet port 54 (FIG. 4) and an interior volume 56. The inlet port 54 is in fluidic communication with the interior volume 56. The interior volume 56 includes a first chamber 58, a second chamber 60, and a third chamber 62. The first chamber 58 is in fluidic communication with the inlet port 54 and the second chamber 60. The second chamber 60 is in fluidic communication with the third chamber 62. A first divider 64 partially separates the first chamber 58 from the second chamber 60. The second divider 66 partially separates the second chamber 60 from the third chamber 62. The first divider 64 causes the first chamber 58 to inflate fully before the second chamber 60 inflates fully, because the first divider 64 partially constrains fluid flow from the first chamber 58 to the second chamber 60. The second divider 66 causes the second chamber 60 to inflate fully before the third chamber 62 inflates fully, for the same reason.

A user can at least partially surround a body part 68 (FIG. 1) of a living being with the compression device 10 and use the source of fluidic pressure 18 to inflate the first inflatable bladder 26, comprising the first chamber 58 (FIG. 4), second chamber 60, and third chamber 62. If the user places the compression device 10 on a body part 68 so that the first chamber 58 is the chamber nearest the heart, then the source of fluidic pressure 18 would inflate the first inflatable bladder 26 to cause compression within the body part 68 in the arterial direction 72 (away from the heart). Alternatively, if the user places the compression device 10 on a body part 68 so that the first chamber 58 is the chamber furthest from the heart, then the source of fluidic pressure 18 would inflate the first inflatable bladder 26 to cause compression within the body part 68 in the venous direction 74 (towards the heart). Again, the source of fluidic pressure 18 can be a pump 38, a connection in a health care facility 40, and/or a pressurized canister 42. The body part 68 could be (but is not limited to) a calf and/or thigh. The compression device 10 could be used to treat or prevent a chronic wound by enhancing circulation, including the direction of blood flow towards the wound, in addition to the other purposes described above.

Figure 6:
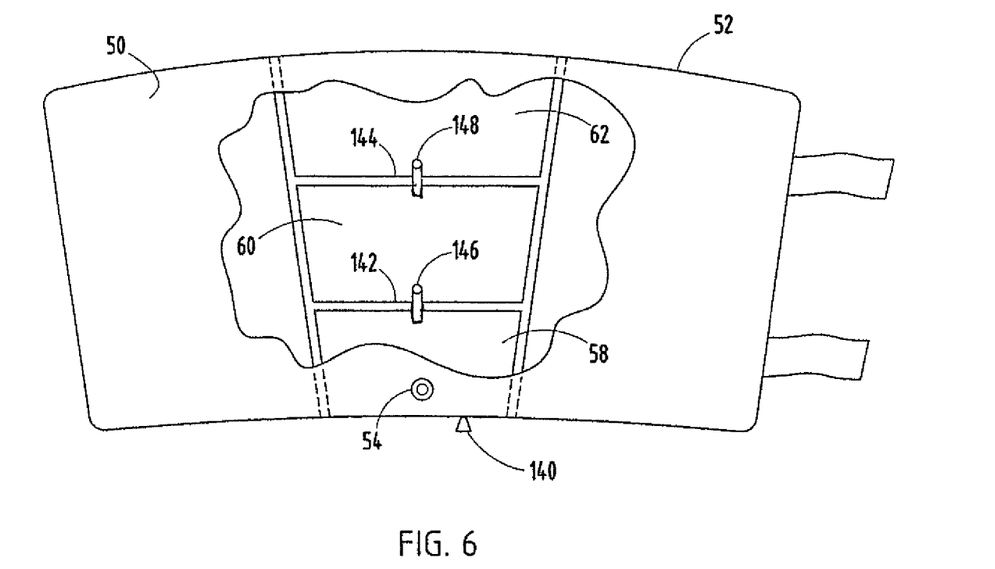
FIG. 6 depicts a front view of inflatable bladder 140, with check valves 146 and 148.

Similarly, the inflatable bladder for the compression device 10 (or any other compression device) can be inflatable bladder 140 (FIG. 6). The inflatable bladder 140 comprises an inlet port 54 in fluidic communication with a source of fluidic pressure 18. The inflatable bladder 140 further comprises a first chamber 58, a second chamber 60, a third chamber 62, a first check valve 146, and a second check valve 148. The first chamber 58 is in fluidic communication with the inlet port 54 and the second chamber 60, through a first check valve 146. The second chamber 60 is in fluidic communication with the third chamber 62, through a second check valve 148. Except for the check valves 146 and 148, dividers 142 and 144 separate the chambers 58, 60, and 62. The first check valve 146 can be a valve set to open at a certain pressure within the first chamber 58, such as 40 mmHg. As fluid from the source of fluidic pressure 18 enters the first chamber 58 through the inlet port 54, the first chamber 58 will undergo inflation until the pressure within the first chamber 58 reaches the pressure required to open the first check valve 146. When the pressure within the first chamber 58 is sufficient, the first check valve 146 will open and allow fluid to enter into the second chamber 60 thus causing the second chamber 60 to begin to undergo inflation. The second chamber 60 will likewise undergo inflation until the pressure within the second chamber 60 reaches the pressure required to open the second check valve 148 (such as 35 mmHg). When that pressure within the second chamber 60 is sufficient, the second check valve 158 will open and allow fluid to enter into the third chamber 62 thus causing the third chamber 62 to begin to under go inflation. The inflatable bladder 140 could have any number of chambers, with separating check valves, and provide the same sequential inflation, as long as the threshold pressure required to open the check valve for a chamber closer to the inlet port 54 is higher than or equal to the pressure required to open the check valve for the next chamber further away from the inlet port 54.

A user can at least partially surround a body part 68 (FIG. 1) of a living being with the compression device 10 (or any other compression device) and use the source of fluidic pressure 18 to inflate the inflatable bladder 140 (FIG. 6), comprising the first chamber 58, second chamber 60, third chamber 62, with check valves 146 and 148. If the user places the compression device 10 on a body part 68 so that the first chamber 58 is the chamber nearest the heart, then the source of fluidic pressure 18 would inflate the first inflatable bladder 26 to cause compression within the body part 68 in the arterial direction 72 (away from the heart). Alternatively, if the user places the compression device 10 on a body part 68 so that the first chamber 58 is the chamber furthest from the heart, then the source of fluidic pressure 18 would inflate the first inflatable bladder 26 to cause compression within the body part 68 in the venous direction 74 (towards the heart). Again, the source of fluidic pressure 18 can be a pump 38, a connection in a health care facility 40, and/or a pressurized canister 42. The body part 68 could be (but is not limited to) a calf and/or thigh. The compression device 10 (or any other) using inflatable bladder 140 could be used to treat or prevent a chronic wound by enhancing circulation, including the direction of blood flow towards the wound (or for any of the other purposes described above).

In a yet another embodiment, a compression device 104 (FIG. 5) includes a housing 48 and a cuff 102. The housing 48 at least partially houses a primary valve 76, access to a source of fluidic pressure 18, and a programmable logic controller 14. The primary valve 76 includes an inlet port 78 in fluidic communication with the source of fluidic pressure 18, and an outlet port 86 in fluidic communication with a manifold 88. The cuff 102 at least partially houses a first bladder 80, a second bladder 90, and a third bladder 96. The first bladder 80 includes a port 82 in fluidic connection with a first valve 84, which in turn is in fluidic connection with the manifold 88. The second bladder 90 includes a port 92 in fluidic connection with a second valve 94, which is in fluidic connection with the manifold 88. The third bladder 96 included a port 98 in fluidic connection with a third valve 100, which is in fluidic connection with the manifold 88. The cuff 102 can house any number of bladders (such as twelve bladders), with the associated ports and valves in connection with the manifold 88, and the three bladders described herein are just an example.

Figure 5:
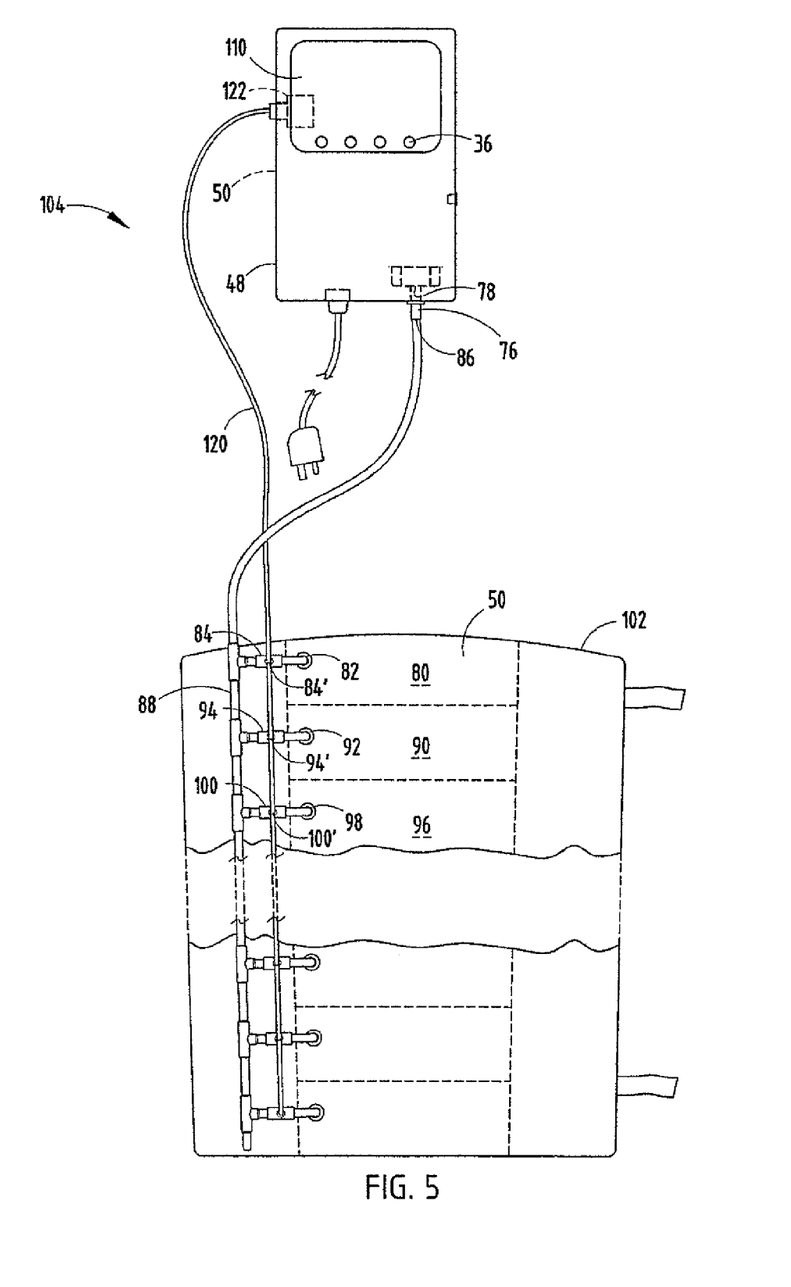
FIG. 5 depicts valves and bladders for the compression device 104.

The programmable logic controller 14 is in electronic connection with the first valve 84, the second valve 94, and the third valve 100. Therefore, the programmable logic controller is capable of selectively controlling the opening and closing of the first valve 84, the inlet valve 94, and the third valve 100. For example, the first, second, and third valves 84, 94, and 100 may each include an addressable controller 84', 94', and 100' such that a single wire pair 120 may serve as a bus and couple all three of the valves to programmable logic controller 14. Programmable logic controller 14 can therefore send a control signal over the wire pair 120 along with the address of the addressable controller associated with the valve to be opened or closed. Additional bladders would of course require additional addressable controllers. By using the above construction, this embodiment represents an improvement over the prior art in that the system may treat all the aforementioned circulatory disorders using the same cuff while using only one air tube per limb and having only a two-wire phone cord 120 or the like per limb coupled to the housing 48.

The source of fluidic pressure 18 can be a pump 38, a connection in a health care facility 40 (FIG. 1), and/or a pressurized canister 42. The cuff 102 can be made from a breathable material such as nylon but need not be.

As with the other embodiments, the housing 48 and cuff 102 for this embodiment (compression device 104) can include an antimicrobial substance 50 (FIG. 5). For example, the antimicrobial substance 50 can include a substance that emits silver-ions, such as a plastic co-molded or co-extruded with a silver-ion emitter (like MCX 122656, manufactured by RTP Co., Winona, Minn.), or a plastic coated or plated with a silver-ion emitted. As other examples, the antimicrobial substance can be one or more of 3 trimethoxysilylpropyloctadecyldimethyl ammonium chloride, hyaluronan and its derivatives, and triclosan. The emission of ions from substances such as the aforementioned aid in the destruction of microbes on a cellular level. The inflatable bladders 26 and 34 (FIG. 3) described in the above embodiments likewise can include such an antimicrobial substance 50.

A user can at least partially surround the body part 68 of a living being with the compression device 104. The user can manipulate the programmable logic controller 14 to activate the source of fluidic pressure 18, open first valve 82 to inflate the first bladder 80, then open the second valve 94 to inflate the second bladder 90, and then open the third valve 100 to inflate the third bladder 96. In this way, the first bladder 80, the second bladder 90, and the third bladder 96 can be inflated sequentially. If the user places the compression device 104 on a body part 68 so that the first bladder 80 is the bladder nearest the heart, then the source of fluidic pressure 18 would inflate the first bladder 80, the second bladder 90, and the third bladder 96 to cause compression within the body part 68 in the arterial direction 72 (away from the heart). Alternatively, if the user places the compression device 104 on a body part 68 so that the first bladder 80 is the chamber furthest from the heart, then the source of fluidic pressure 18 would inflate the first the first bladder 80, the second bladder 90, and the third bladder 96 to cause compression within the body part 68 in the venous direction 74 (towards the heart). Again, the source of fluidic pressure 18 can be a pump 38, a connection in a health care facility 40, and/or a pressurized canister 42. The body part 68 could be (but is not limited to) a calf and/or thigh. The compression device 104 could be used to treat or prevent a chronic wound by enhancing circulation, including the direction of blood flow towards the wound (in addition to the other purpose described above).

The compression device 104 can have any number of bladders, each bladder being in fluidic communication with a port in fluidic communication with a valve, in fluidic communication with the manifold 88. Because each bladder has its own valve, the user can program the programmable logic controller to inflate/deflate any bladder in any sequence or combination, by manipulating the opening/closing the appropriate valve(s).

More generically, a method of treating a wound can comprise the steps of: (i) presenting a body part 68 of a living being 70, the body part 68 having a wound 130 and an area adjacent to the wound 130; (ii) presenting a compression device 10 or 102 (or any other compression device) comprising an inflatable bladder 26 in fluid communication with a source of fluidic pressure 18; (iii) at least partially surrounding the area of the body part 68 adjacent to the wound 130 with the compression device 10 or 102; and (iv) using the source of fluidic pressure to inflate the inflatable bladder 26 to increase circulation in the body part 68. The inflation can be intermittent or non-intermittent. The inflatable bladder 26 need not have the separate chambers described above but can (such as to direct circulation towards the wound) and the compression device 102 need not have separate inflatable bladders as described above but can (such as to direct circulation towards the wound).

Figure 2:
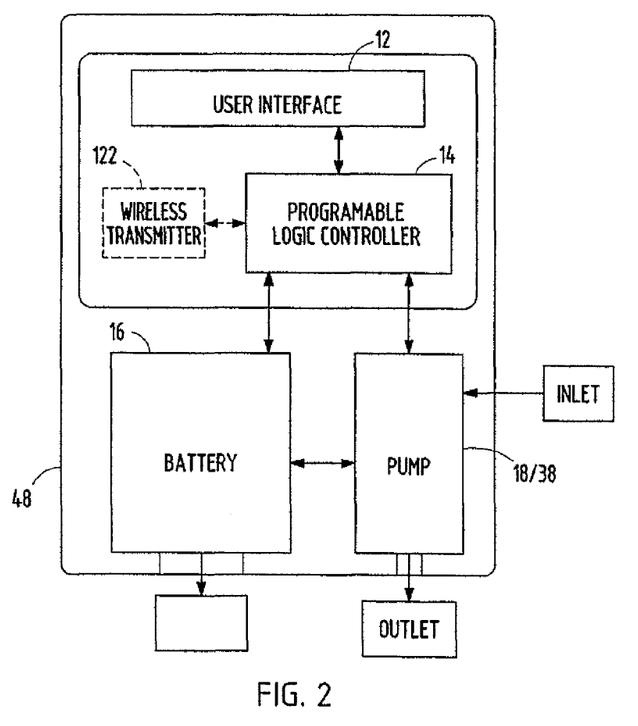
FIG. 2 depicts a block diagram showing the electronic communication between components of one embodiment of the compression device 10.
Figure 3:
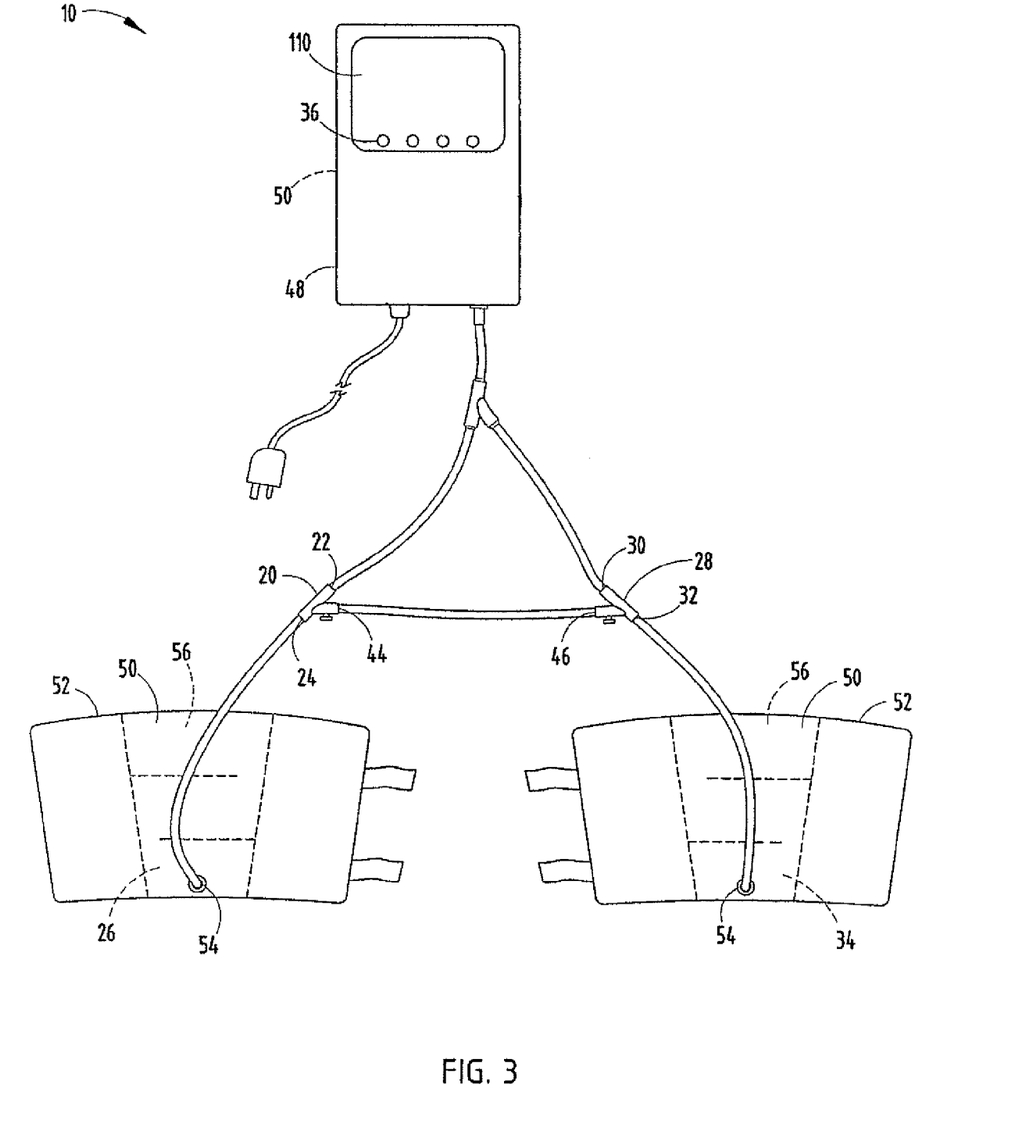
FIG. 3 depicts valves and bladders for several embodiments of the compression device 10.

In all embodiments herein discussed, the housing 48 can further house a wireless transmitter 122 (FIG. 2). The wireless transmitter 122 can transmit pressures, the first period of time, the second period of time, battery power, and other data that the programmable logic controller 14 may measure. A hospital record keeping system (commonly called an EMR system, such as that provided by Cerner) can receive the data transmission from the wireless transmitter 122. All valves having three ports mentioned here-in can be the X-Valve® brand of valve manufactured by Parker Hannifin (Cleveland, Ohio). Pump 38 can be part KPM27C manufactured by Koge Electronics (Xiamen City, China), or a CTS Series pump from Hargraves (Mooresville, N.C.). The pump 38 should be able to provide a pressure of between 0 mmHg and 120 mmHg. The batteries mentioned herein could be rechargeable batteries, such as lithium-ion or nickel-metal hydride (NiMH) batteries. Particular brands of antimicrobial substance 50 include AEGIS, Agion, Biocoat, Silver Shield, Covalon, Zirconium, Microgel, Ecology, Microban, Bio Guard, and RTP Masterbatch 5%.

Various features of the above embodiments may be used in combination. The antimicrobial coated housing 48 and/or cuff 52 may be used with or without any of the other features of the above embodiments.

Although housings 48 are depicted for each of the above embodiments, particularly those for portable battery operated devices, the components housed in housing 48 may be built into a healthcare facility bed or in a control panel for a wall, floor, or ceiling. In this case, the power source may be power from the wall, floor, or ceiling of the healthcare facility. Likewise, the source of fluidic pressure 18 may be an in-wall source of compressed air provided from the healthcare facility.

In the foregoing description, it will be readily appreciated by those skilled in the art that modifications may be made to the invention without departing from the concepts as disclosed herein. Such modifications are to be considered as included in the following claims, unless those claims by their language expressly state otherwise.

What is claimed is:

1. A compression device comprising:
   a user interface;
   a programmable logic controller in electronic connection with the user interface;
   a battery power source in electronic connection with the programmable logic controller;
   a source of fluidic pressure in electronic connection with the programmable logic controller;
   an electrically-actuatable first valve having a first port in fluidic connection with the source of fluidic pressure and a second port in fluidic connection with a first inflatable bladder, the first valve electrically connected to the programmable logic controller;
   an electrically-actuatable second valve having a first port in fluidic connection with the source of fluidic pressure and a second port in fluidic connection with a second inflatable bladder, the second valve electrically connected to the programmable logic controller;
   wherein the programmable logic controller is programmed to cause a repeating sequence of
      i inflating the first inflatable bladder by opening the first and second ports of the first valve, closing the first and second ports of the second valve, and activating the source of fluidic pressure,
      ii after a first period of time, deflating the first inflatable bladder by deactivating the source of fluidic pressure,
      iii inflating the second inflatable bladder by closing the first and second ports of the first valve, opening the first and second ports of the second valve, and activating the source of fluidic pressure,
      iv after a second period of time, deflating the second inflatable bladder by deactivating the source of fluidic pressure, and
   wherein the user interface allows the user to select a first mode or a second mode that extends the life of the battery power source by selecting the first period of time or the second period of time that are longer in length than when the first mode is selected, and
   wherein the user interface allows the user to input a total time of usage when the second mode is selected, and
   wherein the programmable logic controller measures the power remaining in the battery power source, calculates the first period of time and the second period of time based on the total time of usage and the power remaining, and utilizes the first period of time and the second period of time in repeating sequence.

2. The compression device of claim 1, wherein the source of fluidic pressure is a pump.

3. The compression device of claim 1, wherein the source of fluidic pressure is an in-wall source of compressed air of a health care facility.

4. The compression device of claim 1, wherein the source of fluidic pressure is a pressurized canister.

5. The compression device of claim 1, wherein the programmable logic controller continuously re-measures the power remaining in the battery power source, re-calculates the first period of time and the second period of time, and utilizes the first period of time and the second period of time in the repeating sequence.

6. The compression device of claim 1, further comprising a housing, wherein the housing houses the programmable logic controller, and the battery power source.

7. A compression device comprising:
   a user interface;
   a programmable logic controller in electronic connection with the user interface;
   a power source in electronic connection with the programmable logic controller, wherein the power source is a battery;
   a source of fluidic pressure in electronic connection with the power source and the programmable logic controller;
   a first valve having a first port in fluidic connection with the source of fluidic pressure, a second port in fluidic connection with a first inflatable bladder, and a third port in fluidic connection with a second valve;
   the second valve having a first port in fluidic connection with the source of fluidic pressure, a second port in fluidic connection with a second inflatable bladder, and a third port in fluidic connection with the first valve;
   wherein the first inflatable bladder is adapted to be provided on a first leg of the user, and the second inflatable bladder is adapted to be provided on a second leg of the user;
   wherein the programmable logic controller is programmed to cause the repeating sequence of
      i inflating the first inflatable bladder by opening the first and second ports of the first valve, closing the third port of the first valve, closing the first and second ports of the second valve, and activating the source of fluidic pressure,
      ii after a first period of time, deflating the first inflatable bladder and partially inflating the second inflatable bladder by deactivating the source of fluidic pressure, closing the first port of the first valve, opening the third port of the first valve, opening the third port of the second valve, and opening the second port of the second valve,
      iii further inflating the second inflatable bladder by closing the first, second, and third ports of the first valve, opening the first and second ports of the second valve, closing the third port of the second valve, and activating the source of fluidic pressure, and
      iv after a second period of time, deflating the second inflatable bladder and partially inflating the first inflatable bladder by deactivating the source of fluidic pressure, closing the first port on the second valve, opening the third port of the second valve, opening the third port of the first valve, and opening the second port of the first valve, wherein the user interface allows the user to input a total time of usage and the programmable logic controller measures the power remaining in the battery power source, calculates the first period of time and the second period of time based on the total time of usage and the power remaining, and utilizes the first period of time and the second period of time in the repeating sequence.

8. The compression device of claim 7, wherein the source of fluidic pressure is a pump.

9. The compression device of claim 7, wherein the source of fluidic pressure is an in-wall source of compressed air of a health care facility.

10. The compression device of claim 7, wherein the source of fluidic pressure is a pressurized canister.

11. The compression device of claim 7, wherein the programmable logic controller continuously re-measures the power remaining in the battery power source, re-calculates the first period of time and the second period of time, and utilizes the first period of time and the second period of time in the repeating sequence.

12. The compression device of claim 7, further comprising a housing, wherein the housing houses the programmable logic controller, and the power source.

* * * * *